(12) United States Patent
Ren et al.

(10) Patent No.: US 12,714,383 B2
(45) Date of Patent: Aug. 25, 2026

(54) MULTI-MODALITY IMAGING OF A SPECIMEN

(71) Applicant: HOLOGIC, INC., Marlborough, MA (US)

(72) Inventors: Baorui Ren, Marlborough, MA (US); Jay A. Stein, Marlborough, MA (US)

(73) Assignee: Hologic, Inc., Marlborough, MA (US)

(*) Notice: Subject to any disclaimer, the term of this patent is extended or adjusted under 35 U.S.C. 154(b) by 509 days.

(21) Appl. No.: 18/245,151

(22) PCT Filed: Sep. 1, 2021

(86) PCT No.: PCT/US2021/048726
§ 371 (c)(1),
(2) Date: Mar. 13, 2023

(87) PCT Pub. No.: WO2022/066384
PCT Pub. Date: Mar. 31, 2022

(65) Prior Publication Data

US 2023/0355200 A1 Nov. 9, 2023

Related U.S. Application Data

(60) Provisional application No. 63/082,819, filed on Sep. 24, 2020.

(51) Int. Cl.
*A61B 6/00* (2024.01)
*A61B 6/03* (2006.01)
(Continued)

(52) U.S. Cl.
CPC ............ *A61B 6/5235* (2013.01); *A61B 6/032* (2013.01); *A61B 6/502* (2013.01); *A61B 6/5247* (2013.01);
(Continued)

(58) Field of Classification Search
CPC ....... A61B 6/5235; A61B 6/032; A61B 6/502; A61B 6/5247; A61B 8/4416;
(Continued)

(56) References Cited

U.S. PATENT DOCUMENTS 4,038,988 A 8/1977 Perisse
4,134,012 A 1/1979 Smallbone et al.
(Continued)

FOREIGN PATENT DOCUMENTS

DE 20 2019 106 995 1/2020
EP 2277445 1/2011
(Continued)

OTHER PUBLICATIONS

International Search Report and Written Opinion for PCT/US2021/048726 (Dec. 23, 2021).
(Continued)

*Primary Examiner* — Jennifer Mehmood
*Assistant Examiner* — Dustin Bilodeau
(74) *Attorney, Agent, or Firm* — Merchant & Gould P.C.

(57) ABSTRACT

Systems and methods for multi-modality (MMI) imaging of a specimen (136) are disclosed. A specimen may be imaged with a first modality at a first plurality of imaging angles and imaged with a second modality at a second plurality of imaging angles. The first modality may be associated with a different x-ray dose than the second modality. Additionally, one or more angles of the first plurality of imaging angles may be different from the second plurality of imaging angles. Image data obtained from imaging with each modality is used to compile reconstructed images of the specimen. A portion of the reconstructed images that includes a microcalcification may be reconstructed based on image data from the modality associated with a higher dose.

19 Claims, 8 Drawing Sheets

(51) Int. Cl.

| | |
|---|---|
| ***A61B 6/50*** | (2024.01) |
| ***A61B 8/00*** | (2006.01) |
| ***G01N 23/044*** | (2018.01) |
| ***G06T 7/00*** | (2017.01) |
| ***G06V 10/25*** | (2022.01) |

(52) U.S. Cl.

CPC ......... *A61B 8/4416* (2013.01); *G01N 23/044* (2018.02); *G06T 7/0012* (2013.01); *G06V 10/25* (2022.01); *G06T 2207/30068* (2013.01)

(58) Field of Classification Search

CPC ....... A61B 8/0825; A61B 8/5207; A61B 8/15; G01N 23/044; G01N 23/083; G01N 23/046; G06T 7/0012; G06T 2207/30068; G06T 2207/10016; G06T 2207/10116; G06V 10/25

See application file for complete search history.

(56) References Cited

U.S. PATENT DOCUMENTS 4,306,570 A 12/1981 Matthews
4,549,554 A 10/1985 Markham
4,658,834 A 4/1987 Blankenship et al.
4,802,195 A 1/1989 Wojcienchowski
4,803,639 A 2/1989 Steele
4,837,795 A 6/1989 Garrigus
4,852,560 A 8/1989 Hermann, Jr.
5,023,894 A 6/1991 Yamashita
5,023,895 A 6/1991 McCroskey
5,256,160 A 10/1993 Clement
5,427,742 A 6/1995 Holland
5,456,689 A 10/1995 Kresch et al.
5,491,344 A 2/1996 Kenny et al.
5,505,210 A 4/1996 Clement
5,526,822 A 6/1996 Burbank et al.
5,541,856 A 7/1996 Hammermeister
5,575,293 A 11/1996 Miller et al.
5,609,827 A 3/1997 Russell
5,754,621 A 5/1998 Suzuki
5,872,828 A 2/1999 Niklason
5,983,125 A 11/1999 Alfano et al.
6,017,316 A 1/2000 Ritchart et al.
6,032,673 A 3/2000 Savage et al.
6,058,159 A 5/2000 Conway
6,163,590 A 12/2000 Wilkins
6,207,111 B1 3/2001 Weinberg
6,225,107 B1 5/2001 Nagle
6,234,672 B1 5/2001 Tomasetti et al.
6,322,522 B1 11/2001 Zimmon
6,403,035 B1 6/2002 Caratsch et al.
6,485,436 B1 11/2002 Truckai et al.
6,535,284 B1 3/2003 Hajduk et al.
6,646,721 B2 11/2003 Compter
6,882,700 B2 4/2005 Wang
6,899,850 B2 5/2005 Haywood
6,999,554 B2 2/2006 Mertelmeier
7,110,490 B2 9/2006 Eberhard et al.
7,166,113 B2 1/2007 Arambula
7,175,612 B2 2/2007 Felix et al.
7,298,816 B2 11/2007 Moore
7,397,894 B2 7/2008 Nakai
7,453,979 B2 11/2008 Sendai
7,546,925 B1 6/2009 Zuk, Jr.
7,573,977 B2 8/2009 Tsujita
7,616,801 B2 11/2009 Gkanatsios et al.
7,662,109 B2 2/2010 Hibner
7,692,144 B2 4/2010 Watanabe
7,697,661 B2 4/2010 Souchay
7,708,462 B2 5/2010 Fujiwara
7,715,523 B2 5/2010 Lafferty
7,753,857 B2 7/2010 Hibner
7,758,601 B2 7/2010 Heywang-Koebrunner et al.
7,817,773 B2 10/2010 Stanton
7,826,588 B2 11/2010 Eliasson
7,835,490 B2 11/2010 Ramsauer
7,854,705 B2 12/2010 Pawluczyk et al.
7,856,081 B2 12/2010 Peschmann
7,858,038 B2 12/2010 Andreyko et al.
7,867,173 B2 1/2011 Hibner et al.
7,869,563 B2 1/2011 DeFreitas et al.
7,881,427 B2 2/2011 Kalender et al.
7,881,428 B2 2/2011 Jing et al.
7,885,378 B2 2/2011 Kopans
7,972,062 B2 7/2011 Nicolosi
8,038,347 B2 10/2011 Manak
8,038,627 B2 10/2011 Hibner
8,050,735 B2 11/2011 Feke
8,052,616 B2 11/2011 Andrisek et al.
8,162,140 B2 4/2012 Hansen
8,177,728 B2 5/2012 Hibner et al.
8,213,570 B2 7/2012 Panesar
8,217,357 B2 7/2012 Stein et al.
8,235,913 B2 8/2012 Hibner et al.
8,284,896 B2 10/2012 Singh
8,532,745 B2 9/2013 DeFreitas et al.
8,553,837 B2 10/2013 Johansson
8,565,374 B2 10/2013 DeFreitas et al.
8,702,623 B2 4/2014 Parihar
8,741,232 B2 6/2014 Baysal
8,764,679 B2 7/2014 Miller et al.
8,787,522 B2 7/2014 Smith et al.
8,838,207 B2 9/2014 Nakayama et al.
8,873,716 B2 10/2014 Ren et al.
8,911,381 B2 12/2014 Hibner et al.
8,923,603 B2 12/2014 Weston
8,956,306 B2 2/2015 Hibner
8,971,484 B2 3/2015 Beckmann
8,983,030 B2 3/2015 Ookawa
9,020,579 B2 4/2015 Smith et al.
9,066,706 B2 6/2015 DeFreitas et al.
9,068,920 B2 6/2015 Churilla
9,129,715 B2 9/2015 Adler
9,188,696 B2 11/2015 Schafer
9,234,855 B2 1/2016 Watanabe
9,277,895 B2 3/2016 Hara
9,322,790 B2 4/2016 Ookawa
9,326,755 B2 5/2016 Fiebig
9,329,139 B2 5/2016 Itou
9,341,546 B2 5/2016 Stuke
9,347,894 B2 5/2016 Sims
9,492,130 B2 11/2016 Flagle et al.
9,498,175 B2 11/2016 Stein et al.
9,549,709 B2 1/2017 DeFreitas et al.
9,557,281 B2 1/2017 Badawi et al.
9,642,581 B2 5/2017 Lowe
9,668,711 B2 6/2017 Smith et al.
9,733,167 B2 8/2017 Wismueller
9,750,484 B2 9/2017 Finke et al.
9,861,327 B2 1/2018 Yasuda et al.
9,865,424 B2 1/2018 Ikeda
9,901,320 B2 2/2018 DeFreitas et al.
9,943,850 B2 4/2018 Purdy
9,953,799 B2 4/2018 Hakoda
10,008,298 B2 6/2018 King
10,010,296 B2 7/2018 Basu
10,028,717 B2 * 7/2018 Lou ........................ A61B 6/488
10,078,093 B2 9/2018 Flagle
10,098,216 B2 10/2018 Kabumoto
10,105,709 B2 10/2018 Purdy
10,145,806 B2 12/2018 Tanaka
10,190,997 B2 1/2019 Aoki
10,194,875 B2 2/2019 DeFreitas et al.
10,201,331 B2 2/2019 Fleming
10,322,412 B2 6/2019 Purdy
10,393,678 B2 8/2019 Watanabe
10,488,351 B2 11/2019 Butani
10,489,964 B2 11/2019 Wang
10,542,951 B2 1/2020 Klausz et al.
10,561,387 B2 2/2020 Smith et al.
10,631,809 B2 4/2020 Noh
10,646,178 B2 5/2020 Butani
10,652,990 B2 5/2020 Butani

(56) References Cited

U.S. PATENT DOCUMENTS 10,670,545 B2 6/2020 Butani
10,705,030 B2 7/2020 Watanabe
10,709,396 B2 7/2020 Lou
10,729,399 B2 8/2020 Butani
10,729,403 B2 8/2020 DeFreitas et al.
10,753,836 B2 8/2020 O'Driscoll
10,792,003 B2 10/2020 Smith et al.
10,809,208 B2 10/2020 Yashima
10,827,989 B2 11/2020 Vancamberg et al.
10,830,712 B2 11/2020 Butani
10,905,385 B2 2/2021 DeFreitas et al.
10,921,265 B2 2/2021 Butani
10,937,161 B2 3/2021 Butani
11,020,066 B2 6/2021 Butani
11,039,803 B1 6/2021 Butani
11,083,426 B2 8/2021 DeFreitas
11,162,909 B2 11/2021 Butani
11,191,502 B2 12/2021 Smith et al.
11,207,036 B2 12/2021 Butani
11,246,551 B2 2/2022 Butani
11,317,881 B2 5/2022 Purdy et al.
11,358,149 B2 6/2022 Purdy
11,478,206 B2 10/2022 Smith et al.
11,566,981 B2 1/2023 O'Driscoll
11,617,548 B2 4/2023 DeFreitas et al.
11,730,434 B2 8/2023 DeFreitas
11,877,877 B2 1/2024 Purdy
2002/0007188 A1 1/2002 Arambula
2002/0145722 A1 10/2002 Compter
2002/0193656 A1 12/2002 Ravins et al.
2003/0087423 A1 5/2003 Haywood
2003/0216730 A1 11/2003 Barry et al.
2004/0022350 A1 2/2004 Gregerson et al.
2004/0174031 A1 9/2004 Rasmussen
2004/0218716 A1 11/2004 Freifeld
2005/0051723 A1 3/2005 Neagle et al.
2005/0065453 A1 3/2005 Shabaz et al.
2005/0112034 A1 5/2005 McCormick
2005/0124913 A1 6/2005 Damarati
2005/0148842 A1 7/2005 Wang
2006/0074343 A1 4/2006 Hibner
2006/0116603 A1 6/2006 Shibazaki et al.
2006/0173266 A1 8/2006 Pawluczyk et al.
2007/0106176 A1 5/2007 Mark et al.
2007/0116612 A1 5/2007 Williamson
2007/0166834 A1 7/2007 Williamson, IV et al.
2007/0237684 A1 10/2007 Hansen
2007/0239067 A1 10/2007 Hibner et al.
2007/0270714 A1 11/2007 Cushner et al.
2008/0004545 A1 1/2008 Garrison
2008/0082021 A1 4/2008 Ichikawa
2008/0132805 A1 6/2008 Heywang-Koebrunner et al.
2008/0214955 A1 9/2008 Speeg et al.
2008/0221480 A1 9/2008 Hibner et al.
2008/0228103 A1 9/2008 Ritchie et al.
2008/0249434 A1 10/2008 Hashimshony et al.
2009/0088663 A1 4/2009 Miller et al.
2009/0088666 A1 4/2009 Miller et al.
2009/0131818 A1 5/2009 Speeg et al.
2009/0131820 A1 5/2009 Speeg
2009/0131823 A1 5/2009 Andreyko et al.
2009/0171243 A1 7/2009 Hibner et al.
2009/0171244 A1 7/2009 Ning
2009/0213987 A1 8/2009 Stein
2010/0080346 A1 4/2010 Kalender et al.
2010/0081964 A1 4/2010 Mark
2010/0152611 A1 6/2010 Parihar
2010/0160824 A1 6/2010 Parihar
2010/0160826 A1 6/2010 Parihar
2010/0191145 A1 7/2010 Lafferty
2010/0317997 A1 12/2010 Hibner
2011/0123074 A1 5/2011 Nie
2011/0142201 A1 6/2011 Eberhard et al.
2011/0285837 A1 11/2011 Bello
2012/0014504 A1* 1/2012 Jang .................... A61B 6/482 378/37
2012/0051514 A1 3/2012 Sims et al.
2012/0053484 A1 3/2012 Parks
2012/0116246 A1 5/2012 Hibner
2012/0123295 A1 5/2012 Sanbuichi
2012/0245485 A1 9/2012 Hibner
2013/0053724 A1 2/2013 Fiebig
2013/0231585 A1 9/2013 Flagle
2013/0280752 A1 10/2013 Ozcan
2014/0016744 A1 1/2014 Muenker
2014/0039343 A1 2/2014 Mescher
2014/0051986 A1 2/2014 Zhao et al.
2014/0065656 A1 3/2014 Baysal
2014/0072104 A1 3/2014 Jacobsen et al.
2014/0198893 A1* 7/2014 Badawi ............... G01N 23/046 378/19
2014/0257135 A1 9/2014 DeFreitas
2014/0276209 A1 9/2014 Hibner
2015/0083893 A1* 3/2015 Wismueller ............ G01N 1/36 250/453.11
2015/0131773 A1 5/2015 Lowe et al.
2015/0209017 A1 7/2015 Fleming
2016/0211045 A1 7/2016 Jeon et al.
2017/0131311 A1 5/2017 Flagle
2017/0309063 A1 10/2017 Wang
2017/0336706 A1 11/2017 Wang
2018/0045660 A1 2/2018 Yashima
2018/0168523 A1 6/2018 Vancamberg et al.
2018/0249985 A1 9/2018 DeFreitas et al.
2019/0054217 A1 2/2019 Axon
2019/0072463 A1 3/2019 O'Driscoll
2019/0130563 A1 5/2019 Vecchio et al.
2019/0167869 A1 6/2019 Willard
2019/0285558 A1 9/2019 DeFreitas
2019/0346471 A1 11/2019 Flagle
2020/0029927 A1 1/2020 Wilson et al.
2020/0061622 A1 2/2020 Purdy
2020/0085393 A1 3/2020 Zhang et al.
2020/0187923 A1 6/2020 Safir
2020/0268331 A1 8/2020 Purdy
2020/0352543 A1 11/2020 DeFreitas et al.
2020/0386657 A1 12/2020 O'Driscoll
2021/0259649 A1 8/2021 Milioni De Carvalho
2022/0015729 A1 1/2022 Purdy et al.
2022/0015731 A1 1/2022 Liu
2022/0039766 A1 2/2022 DeFreitas
2022/0071583 A1 3/2022 Chmeissani
2022/0110597 A1 4/2022 Chen
2022/0133252 A1 5/2022 Smith et al.
2022/0296189 A1* 9/2022 Purdy ................. A61B 6/4411
2022/0331808 A1 10/2022 Purdy
2023/0012310 A1 1/2023 Stango
2023/0014922 A1 1/2023 DeFreitas
2023/0121010 A1 4/2023 Smith et al.
2023/0136395 A1 5/2023 Chen
2023/0172572 A1 6/2023 Bumdra
2023/0204473 A1 6/2023 O'Driscoll
2023/0404499 A1 12/2023 DeFreitas
2024/0016461 A1 1/2024 Wolff
2024/0315676 A1 9/2024 Chen
2024/0359187 A1 10/2024 Purdy
2025/0072856 A1 3/2025 Bundra

FOREIGN PATENT DOCUMENTS

EP 2007287 6/2016
EP 3143937 3/2017
GB 2018601 10/1979
JP 2006-346179 12/2006
JP 2014-526937 10/2014
JP 2015-085056 5/2015
JP 2015-520402 7/2015
JP 2016-154878 9/2016
JP 2017099928 6/2017
JP 6320717 B2 5/2018
WO 8101363 5/1981
WO 2007021905 2/2007
WO 2008/025146 3/2008

(56) References Cited

FOREIGN PATENT DOCUMENTS

| | | |
|---|---|---|
| WO | 2009/120206 | 10/2009 |
| WO | 2010/028208 | 3/2010 |
| WO | 2011/140374 | 11/2011 |
| WO | 2012/074885 | 6/2012 |
| WO | 2013/166497 | 11/2013 |
| WO | 2017/060726 | 4/2017 |
| WO | 2018/183086 | 10/2018 |
| WO | 2018/204710 | 11/2018 |
| WO | 2019/051496 | 3/2019 |
| WO | 2019/085342 | 5/2019 |
| WO | 2019/216766 | 11/2019 |
| WO | 2020/106888 | 5/2020 |
| WO | 2021/202455 | 10/2021 |

OTHER PUBLICATIONS

Watanabe, M. et al., "The quantitative analysis of thin specimens: a review of progress from the Cliff-Lorimer to the new zeta-factor methods", Journal of Microscopy, vol. 221, No. 2, Feb. 1, 2006, p. 91.

Basak Erguvan-Dogan et al., "Specimen Radiography in Confirmation of MRI-Guided Needle Localization and Surgical Excision of Breast Lesions", American Journal of Roentgenology, American Roentgen Ray Society, vol. 187, No. 2: 339-344 (2006).

PCT International Preliminary Report on Patentability in International Application PCT/US2021/048726, mailed Apr. 6, 2023, 9 pages.

* cited by examiner

MULTI-MODALITY IMAGING OF A SPECIMEN

CROSS-REFERENCE TO RELATED APPLICATIONS

This application is a National Stage Application of PCT/US2021/048726 filed on Sep. 1, 2021, which claims the benefit of priority to U.S. Provisional Patent Application No. 63/082,819, filed on Sep. 24, 2020, the entire disclosures of which are incorporated by reference in their entireties. To the extent appropriate, a claim of priority is made to each of the above disclosed applications.

INTRODUCTION

Lumpectomy techniques are used for removing cancerous or other abnormal tissue from a breast. A lumpectomy is a breast-conserving surgery that removes a portion of the breast. The excised tissue is evaluated for an acceptable margin between any cancerous or abnormal tissue and the exterior surface of the excised tissue.

Imaging of the excised tissue is vitally important to determine if all cancerous or abnormal tissue has been removed from the breast. For example, if any amount of cancerous tissue remains in the breast, cancer cells could grow and otherwise spread throughout the body. Thus, it is important for accurate identification of abnormal tissue and margins when analyzing the excised tissue.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods relating to multi-modality imaging of a specimen. In an aspect, the technology relates to a method for imaging a specimen. The method includes receiving a specimen on a rotatable support surface, wherein the support surface is configured to rotate about an axis. The method further includes rotating the specimen about the axis through a first plurality of imaging angles. While rotating the specimen through the first plurality of imaging angles, the method includes imaging the specimen with a first imaging modality using an imaging source, wherein the imaging source is disposed a fixed distance from the axis. Additionally, the method includes acquiring a first plurality of images of the specimen with the first imaging modality. The method further includes rotating the specimen through a second plurality of imaging angles. While rotating the specimen through the second plurality of imaging angles, the method includes imaging the specimen with a second imaging modality using the imaging source. The method includes acquiring a second plurality of images of the specimen with the second imaging modality, wherein the second imaging modality is different than the first imaging modality. Additionally, the method includes generating a set of reconstructed images of the specimen, wherein the set of reconstructed images is based on both the first plurality of images and the second plurality of images.

In an example, the method further includes securing the specimen to the support surface. In another example, the imaging the specimen with the second imaging modality occurs subsequent to the imaging the specimen with the first imaging modality. In a further example, the first imaging modality is associated with a low x-ray dose and the second imaging modality is associated with a high x-ray dose. In yet another example, the second plurality of images acquired with the second imaging modality associated with the high x-ray dose depict a microcalcification. In still a further example, the first plurality of imaging angles includes at least one angle not included in the second plurality of imaging angles.

In another example, the method further includes evaluating a margin of the specimen based on the set of reconstructed images. In a further example, the method includes displaying at least one reconstructed image of the set of reconstructed images. In yet another example, the first imaging modality and the second imaging modality are selected from the group consisting of: a low-dose CT scan; a high-dose CT scan; a high-dose 2D x-ray exposure; a low-dose tomosynthesis scan; and a high-dose tomosynthesis scan. In still a further example, the first imaging modality is one of a low-dose CT scan or a low-dose tomosynthesis scan, and wherein the second imaging modality is one of: a high-dose CT scan; a high-dose 2D x-ray exposure; and a high-dose tomosynthesis scan. In another example, the rotating the specimen through the first plurality of imaging angles and the rotating the specimen through the second plurality of imaging angles is performed in a single sweep. In a further example, the first imaging modality is the low-dose CT scan and the second imaging modality is the high-dose CT scan. In yet another example, the first imaging modality is the low-dose tomosynthesis scan and the second imaging modality is the high-dose tomosynthesis scan.

In another aspect, a method for imaging a specimen is disclosed. The method includes imaging a breast of a patient with a first imaging modality, the breast including an area of interest and acquiring a first plurality of images of the breast with the first imaging modality. The method also includes excising a specimen from the breast, wherein the specimen includes at least a portion of the area of interest. Additionally, the method includes imaging the specimen with a second imaging modality and acquiring a second plurality of images of the specimen with the second imaging modality. The method further includes imaging the specimen with a third imaging modality and acquiring a third plurality of images of the specimen with the third imaging modality, wherein the third imaging modality is different than the second imaging modality. Additionally, the method includes generating a displayed set of reconstructed images of the specimen, wherein the displayed set of reconstructed images is based on both the second plurality of images and the third plurality of images.

In an example, the first imaging modality is an ultrasound. In another example, the method further includes identifying a margin of the specimen; and removing additional breast tissue based on the identified margin. In a further example, the method includes imaging the breast of the patient with the first imaging modality uses a first imaging source, and wherein imaging the specimen with the second imaging modality and the third imaging modality use a second imaging source. In yet another example, the second plurality of images are acquired over a second plurality of imaging angles and the third plurality of images are acquired over a third plurality of imaging angles, and the second plurality of imaging angles includes at least one angle that is not included in the third plurality of imaging angles.

In yet another aspect, an apparatus for imaging a specimen is disclosed. The apparatus includes: a housing defining an interior chamber; a pedestal disposed within the interior chamber of the housing, wherein the pedestal is configured to support a specimen and rotate about an axis; an imaging source disposed within the housing, the imaging source configured to project a beam inside the interior chamber; a processor; and memory storing instructions that, when executed by the processor, cause the apparatus to perform a set of operations. The set of operations includes rotating the pedestal about the axis through a first plurality of imaging angles. While rotating the pedestal through the first plurality of imaging angles, the set of operations includes imaging with a first imaging modality using the imaging source, wherein the imaging source is disposed a fixed distance from the axis. Additionally, the set of operations includes acquiring a first plurality of images with the first imaging modality. The set of operations also includes rotating the pedestal about the axis through a second plurality of imaging angles. While rotating the pedestal through the second plurality of imaging angles, the set of operations includes imaging the with a second imaging modality using the imaging source. Additionally, the set of operations includes acquiring a second plurality of images with the second imaging modality, wherein the second imaging modality is different than the first imaging modality. The set of operations also includes generating a set of reconstructed images based on both the first plurality of images and the second plurality of images.

In an example, the apparatus further includes a display and wherein the set of operations further includes displaying an image of the set of reconstructed images.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

The accompanying figures illustrate one or more aspects of the disclosed methods and systems for multi-modality imaging of a specimen. In the appended figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label. Non-limiting and non-exhaustive examples are described with reference to the following figures.

Figure 1:
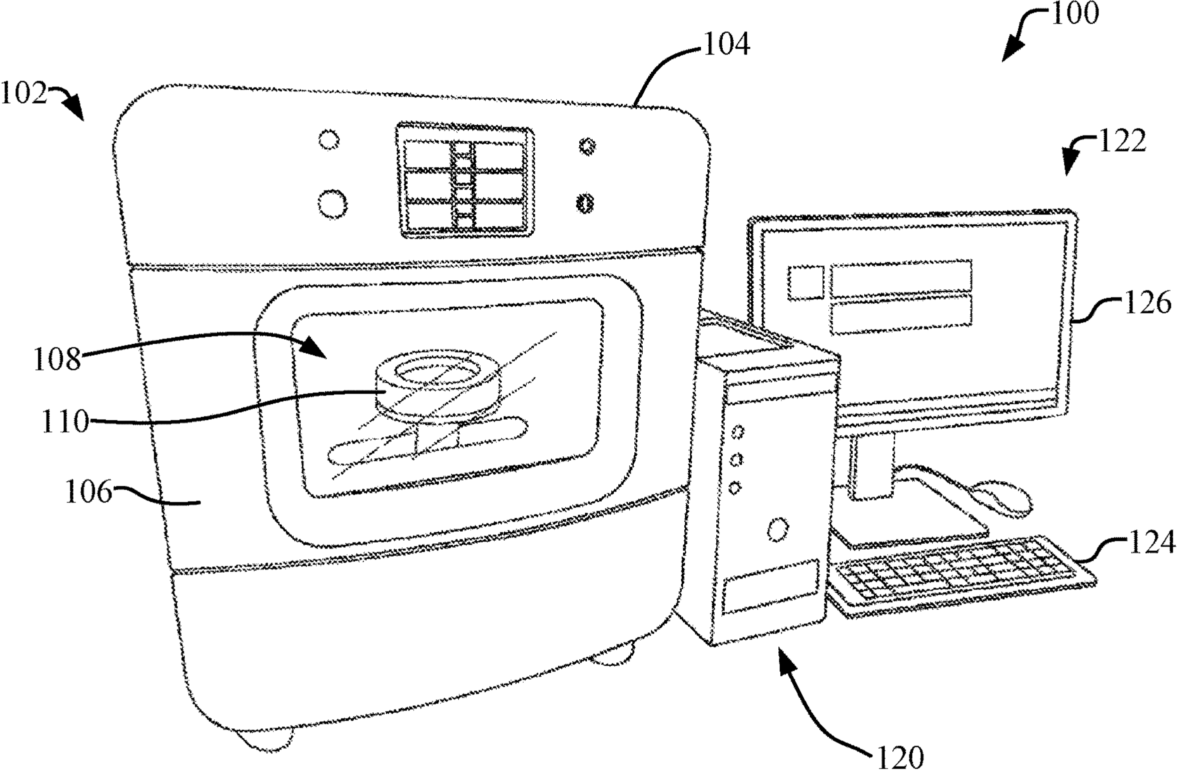
FIG. 1 depicts a specimen imaging system including a shielded imaging cabinet, a computing system, and peripheral devices.

While examples of the disclosure are amenable to various modifications and alternate forms, specific examples have been shown by way of example in the drawings and are described in detail below. The intention is not to limit the scope of the disclosure to the particular examples described. On the contrary, the disclosure is intended to cover all modifications, equivalents, and alternatives falling within the scope of the disclosure and the appended claims.

DETAILED DESCRIPTION

Various aspects of the disclosure are described more fully below, with reference to the accompanying drawings, which show specific example aspects. However, different aspects of the disclosure may be implemented in many different forms and should not be construed as limited to the aspects described herein; rather, these aspects are provided so that this disclosure will be thorough and complete, and will fully convey the scope of the aspects to those skilled in the art. Aspects may be practiced as methods, systems, or devices. The following detailed description is, therefore, not to be interpreted in a limiting sense.

Imaging a tissue specimen (e.g., tissue excised from a breast) allows for margin assessment about a lesion contained in the specimen. When analyzing margins, an image is taken of the whole specimen, as received. The image may be an x-ray image, optical image, infrared image, contrast enhanced image, and/or other image type taken using known imaging modalities (e.g., computerized tomography (CT), MRI, ultrasound, fluoroscopy, PET, tomosynthesis, or any other imaging modality).

Specimen imaging systems offer structures to image excised tissue utilizing an image type and image modality. An example of a specimen imaging system is the Hologic Faxitron 3D breast specimen-designated computerized tomography (CT) system, VisionCT®, which offers 360-degree images of excised lesions to provide better margin assessments and surgical outcomes. A CT-based specimen imaging system has advantages over other imaging systems, including high isotropic spatial resolution in 3D, high low-contrast detectability (LCD), little to no tissue overlapping, 3D volume rendering and display capability, and quantitative tissue imaging. To realize these advantages from a CT scan, however, a high imaging dose is needed. Higher doses require a longer time for the imager to deliver the dose, thus increasing total time for image acquisition. For a specimen imaging system with a typical fixed-target micro-focus x-ray tube, the imaging time to deliver the high dose associated with a 360-degree CT scan is approximately 180 seconds, plus additional image processing time. Additionally, at higher doses, an x-ray tube may require a longer period of time to cool between obtaining images, thus also increasing image acquisition time and delays between imaging different specimens. Moreover, images acquired at higher doses are often associated with higher resolution image data, which may increase image processing time post-acquisition.

Reducing the imaging time is clinically advantageous. For example, reducing the imaging time increases the quantity of images obtained over time and thus increases clinical throughput in the operating room. This may be advantageous because specimens may be imaged immediately upon removal and, if it is determined that the margins are not sufficient, further removal of tissue may be performed during the same removal procedure. One way to reduce scan time is to use a more powerful imaging source (e.g., x-ray tube) to deliver the dose in a shorter time. Additionally or alternatively, imaging time may be reduced by altering the method and/or varying the mode of imaging. As an example, the imaging the specimen utilizing multi-modal imaging techniques may reduce imaging time.

Accordingly, the present disclosure provides systems and methods for multi-modal imaging of a specimen that, in part, promotes accuracy and efficiency for specimen imaging.

Multi-modality imaging (MMI) may be used to provide different imaging data for specific aspects or features of breast tissue. For example, soft tissue and micro-calcifications may require imaging at unique resolution and/or dose level to provide clinically relevant image quality. Image processing techniques and algorithms may be used to combine images obtained using different modalities to produce final images that include image data for both masses (e.g., as shown in soft tissue) and micro-calcifications. MMI of breast tissue may be used during regular screening or diagnostic imaging of a patient's breast, for example, prior to any invasive or extractive procedures (e.g., biopsies, lumpectomies, etc.) being performed. One example of MMI performed on a breast of a patient is a combination of mammogram and tomosynthesis procedures performed as part of a regular breast cancer screening procedure.

Aspects of MMI techniques used for breast imaging may be applied to specimen imaging to reduce dose and imaging time, while maintaining or improving quality of reconstructed images. As used herein, the term "specimen imaging" contemplates the imaging of a specimen of tissue (e.g., breast tissue) after said tissue is removed from the breast. By using MMI for a specimen, isotropic high resolution may be obtained for a subset of a 360-degree scan, with lower dose and resolution at other angles where high resolution is not required or desired. Additionally or alternatively, resolution may be varied between a planar direction and slice direction. Moreover, imaging angles that include a portion of a micro-calcification, which is more easily viewed under high dose, may be performed at higher doses, while imaging angles including soft tissue and mass-like lesions, which is more easily viewed under low dose, may be imaged at a relatively lower dose. By limiting the amount of images acquired at high dose, overall dose may be lowered and image acquisition time and image processing time may be reduced.

For example, a specimen may be imaged with a first modality at a first plurality of imaging angles and imaged with a second modality at a second plurality of imaging angles. The first modality may be associated with a different x-ray dose than the second modality. Additionally, one or more angles of the first plurality of imaging angles may be different from the second plurality of imaging angles. Image data obtained from imaging with each modality is used to compile reconstructed images of the specimen. A portion of the reconstructed images that includes a micro-calcification may be reconstructed based on image data from the modality associated with a higher dose.

Figure 2:
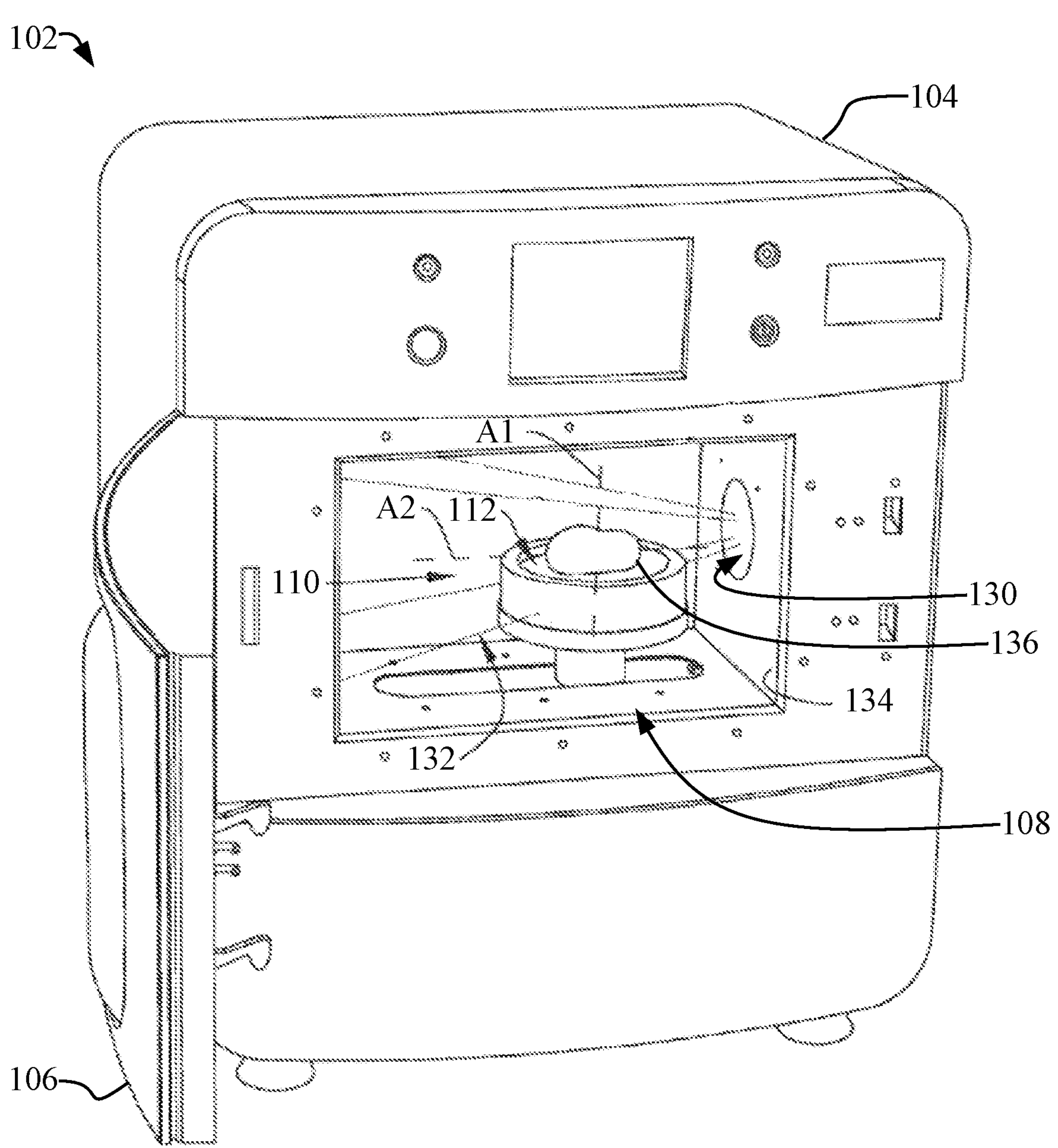
FIG. 2 depicts the shielded imaging cabinet of FIG. 1 including an interior chamber with a pedestal for receiving a specimen and an imaging source.

FIG. 1 depicts a specimen imaging system 100 including a shielded imaging cabinet 102, a computing system 120, and peripheral devices 122. Examples of a specimen imaging system are provided in PCT International Patent Application PCT/US2019/062481, filed on Nov. 20, 2019, the disclosure of which is hereby incorporated by reference herein in its entirety. The shielded imaging cabinet 102 may include a housing 104 that generally defines an interior chamber 108 for receiving an object (e.g., a tissue specimen excised from breast tissue) at a pedestal 110. The interior chamber 108 may be accessed via a shielded access member 106 (e.g., door) in the housing 104. The interior chamber 108 may have any appropriate arrangement of walls (e.g., sidewalls, top walls, and bottom walls). The shielded access member 106 is movably coupled to the housing 104 between a closed position (e.g., as shown in FIG. 1) and an open position (e.g., as shown in FIG. 2), to provide access to the interior chamber 108. The housing 104 and the shielded access member 106 may be made of a material designed to contain sound, radiation, and/or energy emitted from an imaging source inside of the interior chamber 108 to prevent or reduce escape outside of the housing 104.

The pedestal 110 may be movable and rotatable relative to the housing 104 of the cabinet 102. The pedestal 110 may be configurable to receive an object (e.g., tissue specimen), such that the object moves with the pedestal 110 and is thus movable and rotatable relative to the housing 104 and walls of the interior chamber 108. The pedestal 110 may be at least partially constructed from any appropriate radiolucent or echogenic material to reduce the appearance of the pedestal 110 in an image constructed using an imaging source (e.g., imaging source 130) inside the cabinet 102.

The computing system 120 (e.g., including processor(s), memory, etc., as further described below in FIG. 6) may be communicatively coupled and/or electrically coupled with peripheral devices 122, including an input device 124 and a display 126. The computing system 120 may be configured to receive input from a medical professional at an input device 124 (e.g., keyboard, mouse, touchscreen, etc.). Input received at an input device 124 may cause the computing system 120 to initiate an imaging procedure using the cabinet 102. An imaging procedure may include moving and/or rotating the pedestal 110 and/or an object (e.g., tissue specimen) positioned at the pedestal 110 relative to an imaging source inside of the housing 104, emit and receive signals from the imaging source, process the signals from the imaging source, and generate various 2D and/or 3D images of the object for presentation to the medical professional (e.g., at display 126) or for use in margin identification and evaluation. The imaging procedure may include imaging the object with a plurality of imaging types or imaging modalities. In such an instance, the comping system 120 may also perform an image processing technique to combine image data obtained from the plurality of imaging types and/or imaging modalities into a set of reconstructed images of the object.

Although the computing system 120 is illustrated as a separate unit from the cabinet 102, the computing system 120 may be housed within the housing 104 of the cabinet 102 in a single unit or may be disposed remote from the cabinet 102 such as in a separate room or in a geographically remote location. In either instance, the computing system is communicatively coupled with the cabinet 102 (e.g., wired or wirelessly via one or more networks or servers) using processor(s) that are configured to execute one or more sets of computer-readable instruction sets to carry out the various determinations and functionalities disclosed herein (e.g., positioning and/or rotating the pedestal 110 within the interior chamber 108, triggering an imaging source to emit a beam through an object positioned at the pedestal 110, generating image data with a plurality of imaging modalities, etc.).

FIG. 2 depicts the shielded imaging cabinet 102 of FIG. 1 including the interior chamber 108, with the pedestal 114 for receiving a specimen 136 and an imaging source 130. The pedestal 110 may include a receiving surface 112 at which a specimen 136 is positioned. The specimen 136 may be gravitationally seated on the receiving surface 112 of the pedestal or otherwise removably coupled to the receiving surface 112 of the pedestal 110 (e.g., with a coupling member or structure), such that the specimen 136 moves with movement of the pedestal 110. Alternatively, the receiving surface 112 of the pedestal 110 may rotate relative to the pedestal 110, such that the specimen 136 may move with movement of the receiving surface 112. The specimen 136 may be centered on the pedestal 110 and/or receiving surface 112 or may be off-center. Additionally, the specimen 136 may be oriented relative to the pedestal 110 based on a location of the imaging source 130 relative to the pedestal 110 (e.g., a distance between the center of the specimen 136 and the imaging source 130) and a location of a lesion in the specimen 136 (e.g., orientation of the specimen 136 relative to the imaging source 130), to allow imaging of the lesion in the specimen 136 from a particular direction, such as to identify margins around a lesion in a particular direction.

As further described herein, the pedestal 110 and/or receiving surface 112 may rotate about a rotation axis A1. The rotation axis A1 may be centered with the pedestal 110 and/or receiving surface 112, such that the center of the pedestal 110 and/or receiving surface 112 remains fixed at the rotation axis A1 while rotating. Alternatively, the rotation axis A1 may be off-center from the pedestal 110 and/or receiving surface 112, such that the center of the pedestal 110 and/or receiving surface rotates about the rotation axis A1 when rotating. The rotation axis A1 may be fixed distance from the center of the pedestal 110 and/or receiving surface 112 such that movement of the pedestal 110 and/or receiving surface 112 within the interior chamber 108 also moves the rotation axis A1 within the interior chamber 108. When rotating the pedestal 110 and/or receiving surface 112 about the rotation axis A1, the rotation axis A1 may be a fixed distance relative to the imaging source 130 and/or the center of the pedestal may be a fixed distance relative to the imaging source 130 and/or the center of the receiving surface may be a fixed distance relative to the imaging source 130 and/or the center of the specimen 136 may be a fixed distance relative to the imaging source 130 (e.g., if the specimen 136 is centered on the pedestal 110 and/or receiving surface 112).

The imaging source 130 may be non-movably coupled to a portion of the housing 104 and/or a beam sidewall 134 of the interior chamber 108. The imaging source 130 emits a beam 132 (e.g., x-ray, ultrasound, etc.) to be received at a detector (e.g., in the case of an x-ray beam 132 the detector may be coupled to a sidewall opposite of the beam sidewall 134, or in the case of an ultrasound beam 132 the detector may be coupled to the beam sidewall 134). A plurality of imaging sources 130 may be housed in the cabinet 102 and may be located at different locations within the housing 104. The beam 132 emitted from the imaging source 130 may travel along an imaging axis A2 through a portion of the specimen 136 and/or a portion of the pedestal 110. The beam 132 may expand symmetrically about the imaging axis A2 as the beam travels from its origination at the imaging source 130 (e.g., in the shape of cone or a pyramid).

Figure 3A:
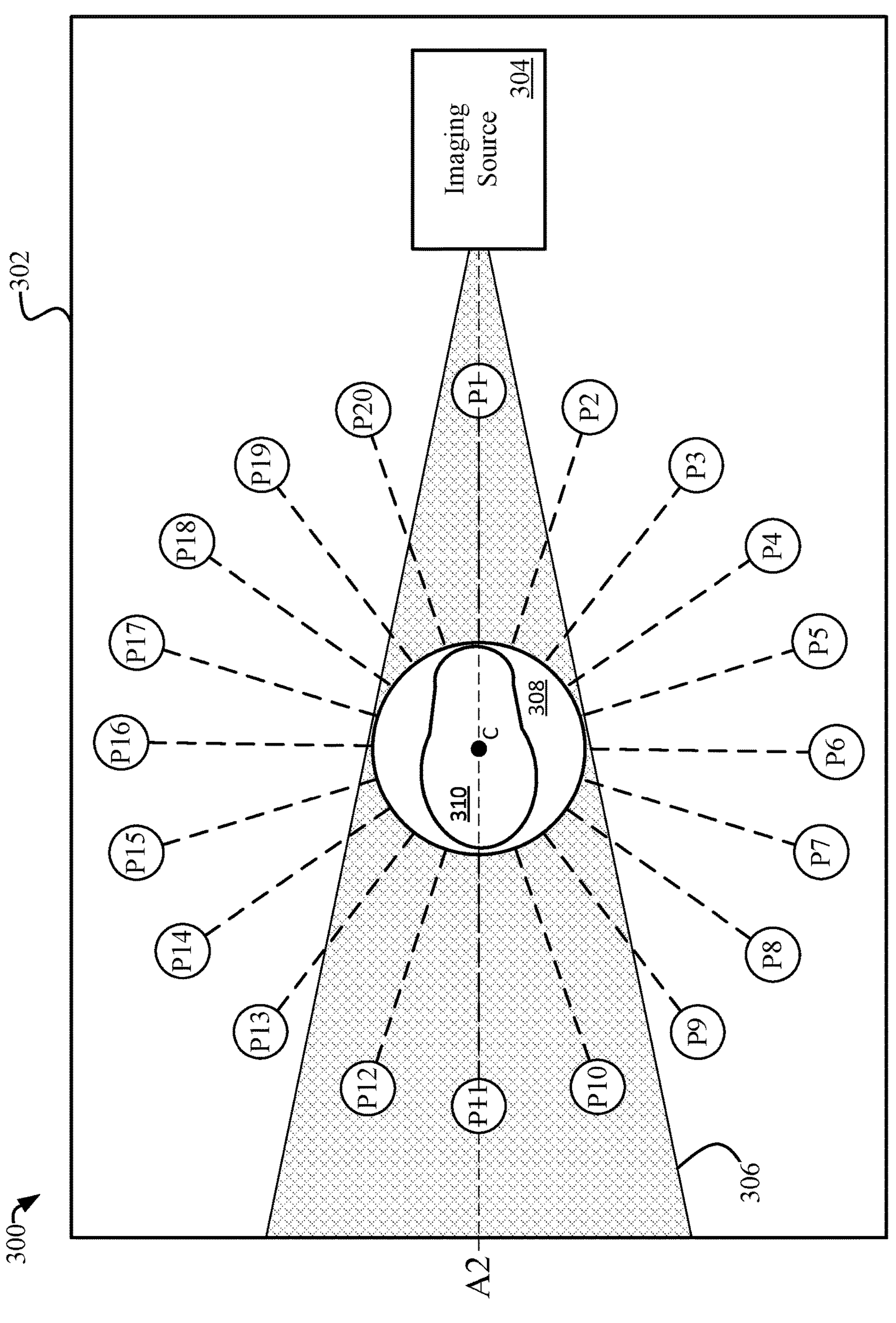
FIGS. 3A-C depict a top-down view of an imaging system including a movable and rotatable pedestal and an imaging source.
Figure 3B:
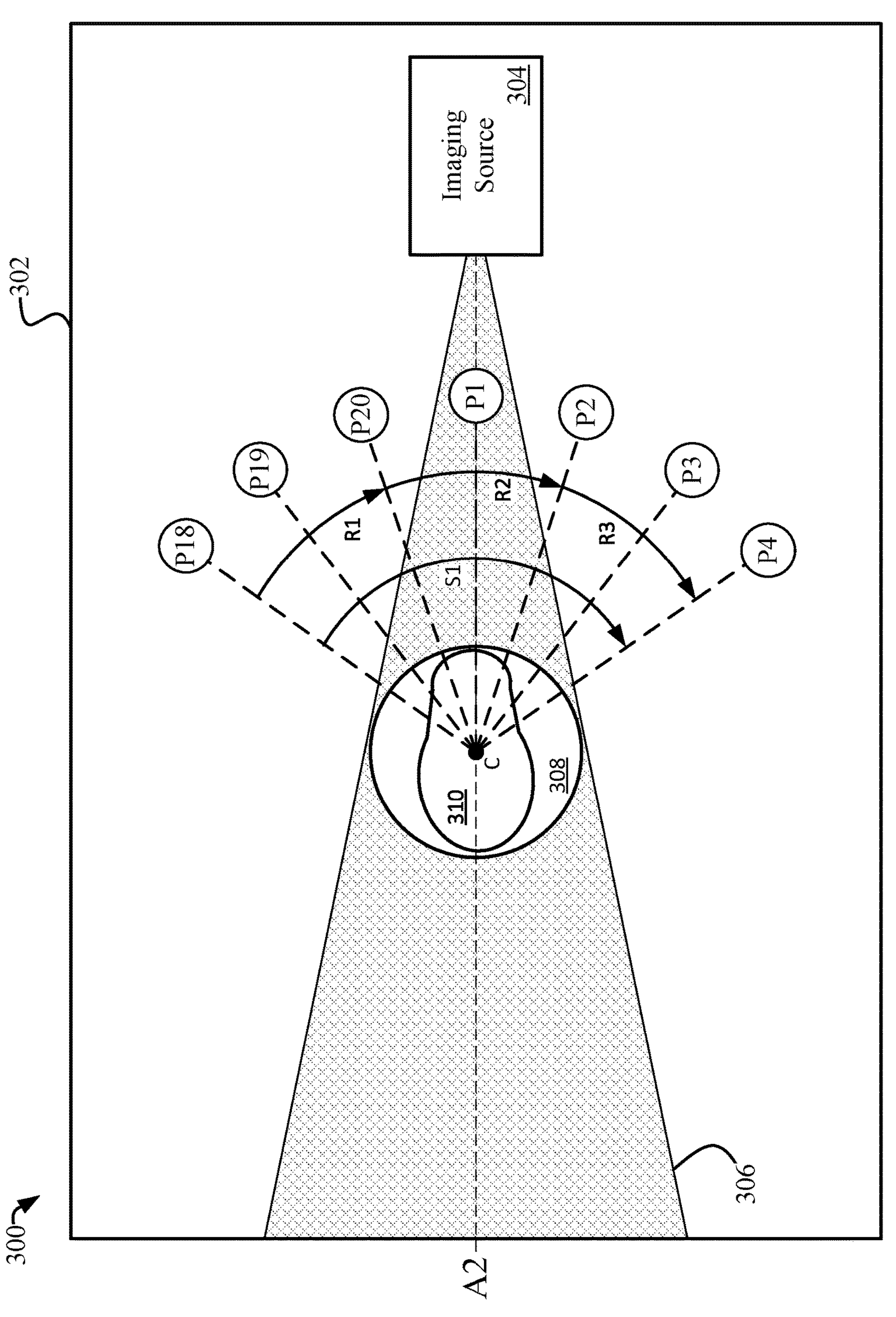
Figure 3C:
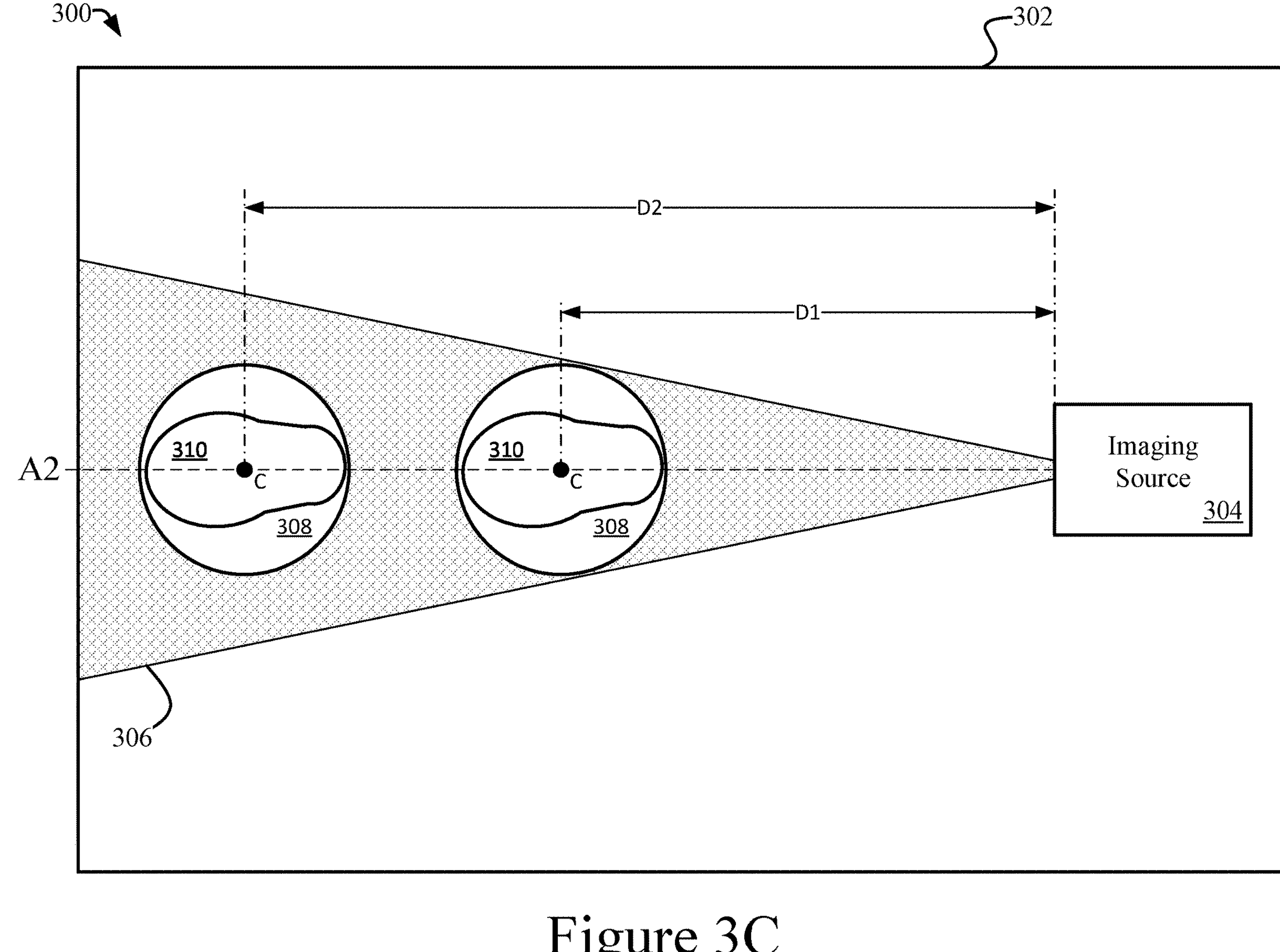

FIGS. 3A-C depict a top-down view of an imaging system 300 including a movable and rotatable pedestal 308 and an imaging source 304. The imaging system 300 may have similar features as the system 100 shown in FIG. 1. For example, a pedestal 308 and an imaging source 304 may be contained within an interior chamber 302 of an imaging system 300 (e.g., a cabinet and/or a computing system).

As shown in FIG. 3A, the pedestal 308 and the specimen 310 may share a center C about which the pedestal 308 rotates (e.g., a rotation axis A1 of the pedestal 308 intersects the center C of the pedestal 308). The imaging axis A2 defines the axis along which a beam 306 travels, as emitted from the imaging source 304. As shown in FIG. 3A, the imaging axis A2 intersects the center C of the pedestal 308. Although the example shown depicts alignment of the center C of the pedestal with the center C of the specimen 310 with the imaging axis A2 and the rotation axis A1 (e.g., travelling through center C), any arrangement of the specimen 310, pedestal 308, imaging axis A2, and rotation axis A1 that allows for at least a portion of the beam 306 to intersect at least a portion of the specimen 310 should be appreciated. The rotation axis A1, imaging axis A2, and center C are all depicted aligned with center C in FIGS. 3A-C, for simplicity and clarity.

As further described herein, the pedestal 308 (or a portion thereof) is rotatable about a rotation axis A1 (as shown, rotatable about center C). The center C of the pedestal 308 (and, in this case, the center C of the specimen 310) may be a fixed distance from the imaging source 304 while rotating about the center C. The pedestal 308 may rotate relative to the imaging source 304 through a plurality of imaging angles at a respective plurality of rotation positions. The rotation of the pedestal 308 may be clockwise, counterclockwise, or both (e.g., a motor that rotates the pedestal 308 may rotate in both directs to reduce wear on the motor). As shown in FIG. 3A, the pedestal 308 is rotatable through twenty rotation positions (P1-P20). As used herein, a rotation position P1-P20 is a position to which the pedestal 308 may be rotated about a rotation axis A1 relative to the imaging source 304 to a relative imaging angle at that rotation position. The imaging system 300 may have a home position for pedestal 308. For example, a home position may include a home distance between the center C of the pedestal 308 and the imaging source 304 and/or a rotational orientation of the pedestal rotated to a home position (e.g., position P1 associated with a 0-degree imaging angle).

Unlike imaging of tissue within the patient (e.g., breast imaging using tomosynthesis, CT, etc.), where the tissue remains fixed while the imaging source rotates, specimen imaging may be performed with a fixed imaging source and movement and/or rotation of the specimen. For specimen imaging, movement and/or rotation of the specimen may be desirable over movement and/or rotation of the imaging source to reduce equipment footprint (as more space is required to move the imaging source), and more easily contain imaging beams. In contrast, for breast imaging, movement and/or rotation of the imaging source may be desirable over movement and/or rotation of the breast tissue to limit breast twisting, reduce equipment footprint (as more space is required to move a patient about an imaging source), and increase imaging accuracy (by maintain a common position of the patient over multiple images).

The rotation positions P1-P20 may be symmetrically spaced such that each rotation position P1-P20 is a same, fixed angle apart (e.g., in this example each rotation position P1-P20 is 18 degrees apart, in another example, each rotation position may be one degree apart, 1.5 degrees apart, 2 degrees apart, etc.). Alternatively, the rotation positions P1-P20 may be separated by uneven angles (e.g., a first angular spacing for a first portion of angles and a second angular spacing for a second portion of angles, such as one-degree angular spacing for a 60-degree range and a five-degree angular spacing for the remaining 300 degrees) or at predetermined angles or user-specified angles. Although twenty rotation positions P1-P20 are shown in this example, any number of rotation positions about a 360-degree rotation should be appreciated.

When imaging the specimen 310 using the imaging system 300, the pedestal 308 may rotate through a plurality of rotation positions (e.g., a subset of the rotation positions P1-P20), while being imaged at each rotation position of the plurality of rotation positions. Aspects of the image taken at each of the plurality of rotation positions may vary (e.g., x-ray dose, dose time, beam type such as x-ray or ultrasound, etc.). The plurality of rotation positions at which the specimen 310 is imaged on the pedestal 308 and/or aspects of the image taken at each of the plurality of rotation positions may be based on a specified or selected image modality.

Imaging modalities may include a CT scan, a 2D x-ray exposure (e.g., radiographic exposure), a tomosynthesis scan, an ultrasound image, and any other imaging modality. A CT scan includes imaging at a plurality of rotation positions spanning at least 180 degrees or more. In an example, a CT scan may include imaging at imaging angles at respective rotation positions radially spaced every one degree for a 360-degree sweep of the pedestal 308. As used herein, a "sweep" refers to consecutive images taken as the pedestal 308 is rotated in one direction (e.g., clockwise or counterclockwise). A 2D x-ray exposure is imaging at one, single imaging angle at a relative rotation position (e.g., at a specified angle or specified rotation position P1-P20). For example, a 2D radiograph exposure may be taken at position P3. A tomosynthesis scan may be wide-angle or narrow-angle. A wide-angle tomosynthesis scan includes imaging at a plurality of rotation positions, e.g., spanning 10-180 degrees, although other angular ranges such as 15-90 degrees, 15-60 degrees, 15-30 degrees, 30-90 degrees, 30-60 degrees, or 40-80 degrees are contemplated. For example, a wide-angle tomosynthesis scan may include imaging at imaging angles at respective rotation positions radially spaced every one degree for a 60-degree sweep. A narrow-angle tomosynthesis scan includes imaging at a plurality of rotation positions, e.g., spanning 0-60 degrees, although other angular ranges such as 5-30 degrees, 5-15 degrees, 10-60 degrees, 10-30 degrees, and 10-20 degrees, are contemplated. For example, a narrow-angle tomosynthesis scan may include imaging at imaging angles at respective rotation positions radially spaced every one degree for a 15-degree sweep. Although the above examples include imaging every one degree, imaging at other symmetrically or asymmetrically spaced angles should be appreciated. For example, images may be taken every 1.5 degrees, two degrees, three degrees, etc., or may be taken every one degree for a first portion of the sweep and every two degrees (or any rotation other than one degree) for a second portion of the sweep.

To reduce the amount of time required to obtain images of the specimen without sacrificing image quality of micro-calcification(s) and tissue mass(es), a variety of x-ray doses may be used (i.e., where the imaging source 304 emits an x-ray beam 306). In an example, the specimen 310 may be imaged with a first modality at a lower dose and imaged with a second modality at a higher dose. Alternatively, the specimen 310 may be imaged with a single modality (which may have a varying dose, as may vary based on the imaging angle at a respective rotation position, i.e., the angle that the specimen 310 is oriented relative to the imaging source 304). As another alternative, the specimen 310 may be imaged with one or more modalities while skipping (i.e., not imaging at) specified imaging angles at respective rotation positions. Images taken with a higher dose provide image data for micro-calcification(s) (e.g., for boundary identification and margin identification), to be overlaid onto the lower dose image data. Example combinations of imaging modalities and/or x-ray dose variability include, but are not limited to, the following example configurations.

Configuration 1: A low-dose CT scan and one or more high-dose 2D x-ray exposure(s). Micro-calcification image data is extracted from the high-dose 2D x-ray exposure(s) and overlaid onto the low-dose image data from the CT scan.

Configuration 2: A low-dose CT scan and a high-dose narrow-angle tomosynthesis scan. Micro-calcification image data is extracted from the high-dose narrow-angle tomosynthesis scan and overlaid onto the low-dose image data from the CT scan.

Configuration 3: A low-dose wide-angle tomosynthesis scan and a high-dose narrow-angle tomosynthesis scan. Micro-calcification image data is extracted from the high-dose narrow-angle tomosynthesis scan and overlaid onto the image data for the low-dose wide-angle tomosynthesis scan.

Configuration 4: A low-dose wide-angle tomosynthesis scan and one or more high-dose 2D x-ray exposure(s). Micro-calcification image data is extracted from the high-dose 2D x-ray exposure(s) and overlaid onto the image data for the low-dose wide-angle tomosynthesis scan.

Configuration 5: A single-sweep CT scan over a plurality of rotation positions with a first portion of the plurality of rotation positions imaged at a high dose and a second portion of the plurality of rotation positions imaged at a low dose. A third portion of the plurality of rotation positions may optionally be skipped. Micro-calcification image data is extracted from the high-dose first portion and combined with image data from the low-dose second portion.

Configuration 6: A single-sweep wide-angle tomosynthesis scan over a plurality of rotation positions with a first portion of the plurality of rotation positions imaged at a high dose and a second portion of the plurality of rotation positions imaged at a low dose. A third portion of the plurality of rotation positions may optionally be skipped. Micro-calcification image data is extracted from the high-dose first portion and combined with image data from the low-dose second portion.

Other configurations and combinations of imaging modalities and/or x-ray doses at any number of rotation positions should be appreciated over any quantity of sweep(s). For the above configurations, the imaging modalities may be employed in any order. Although not included in the above configurations, more than two modalities may be implemented.

FIG. 3B shows the top-down view of an imaging system 300 of FIG. 3A with the rotatable pedestal 308 rotating through a single sweep S1. The single sweep S1 may include a plurality of subranges (e.g., a first range R1, a second range R2, and a third range R3). Although three subranges are shown, any number of subranges should be appreciated. Each subrange may be imaged at a different dose. For example, the first range R1 of the single sweep S1 may be imaged at a low dose, the second range R2 of the single sweep S1 may be imaged at a high dose, and the third range R3 may be imaged at the low dose. In an example, the first range R1 spans 15-30 degrees (e.g., 23 degrees), the second range R2 spans 10-20 degrees (e.g., 15 degrees), and the third range R3 spans 15-30 degrees (e.g., 22 degrees). In another example, the subranges of the single sweep S1 may be the same angle range (e.g., the first range R1, the second range R2, and the third range R3 each spanning 15 degrees).

FIG. 3C shows the top-down view of an imaging system 300 of FIG. 3A with the rotatable pedestal 308 imaged a source-to-axis distance (SAD) (e.g., distance D1 and distance D2). The SAD may be changed while performing sweeps or in between sweeps. A magnification of an image may be based on the SAD. Additionally, a dose may be based on the SAD. For example, the closer the specimen 310 to the imaging source 304 (e.g., the shorter the SAD), the stronger the magnification and the dose. Thus, a shorter SAD may increase imaging dose without adding more stress to the imaging source 304 (e.g., the x-ray tube). In an example, after a first scan at a first SAD D1 the rotatable pedestal 308 may be adjusted to a second SAD D2. The first SAD D1 may be shorter than the second SAD D2, or vice versa. For instance, the SAD may be adjusted to switch to high magnification mode by moving the rotatable pedestal 308 closer to the imaging source 304 (e.g., at first SAD D1).

Figure 4:
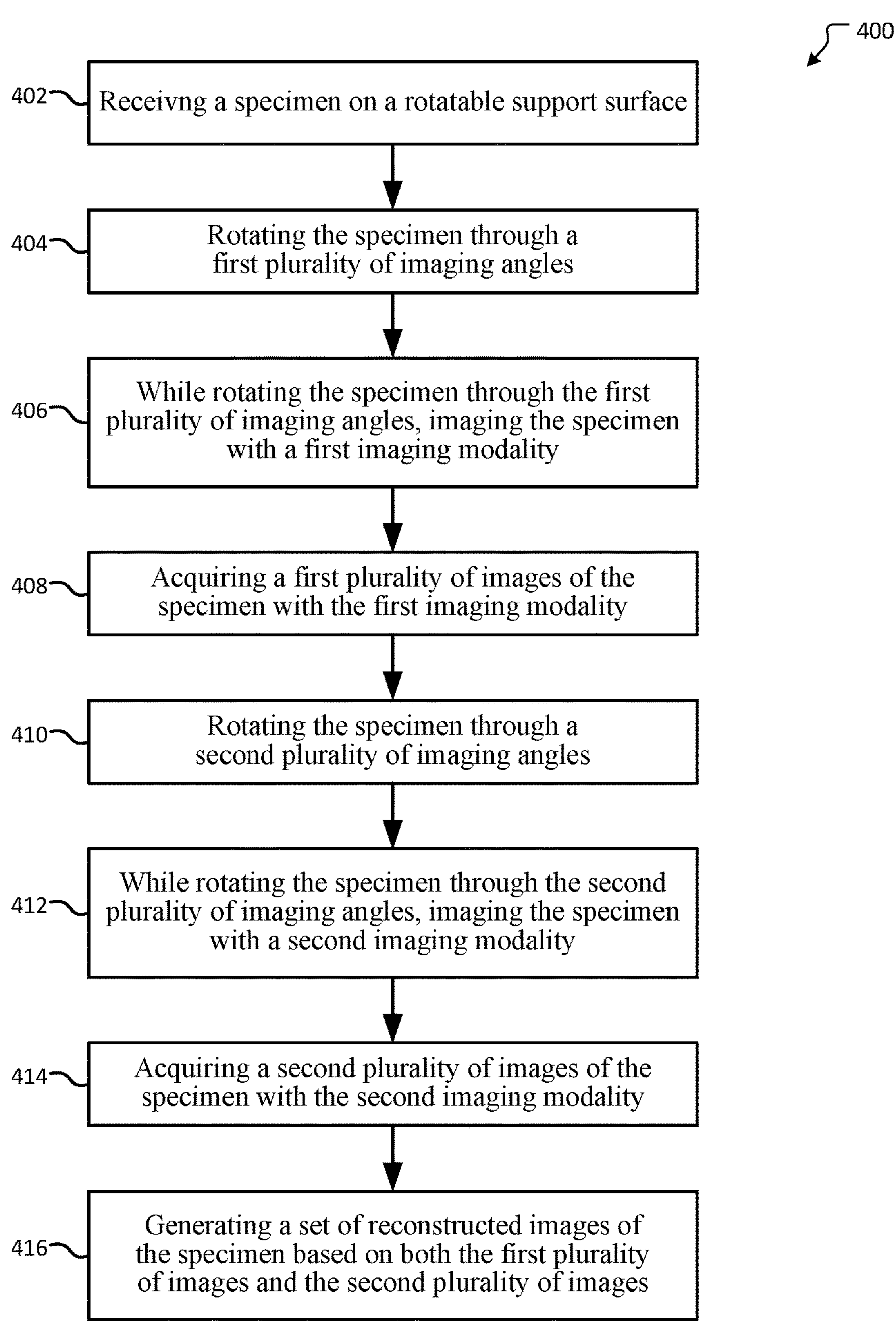
FIG. 4 depicts an example method for multi-modality imaging of a specimen.
Figure 5:
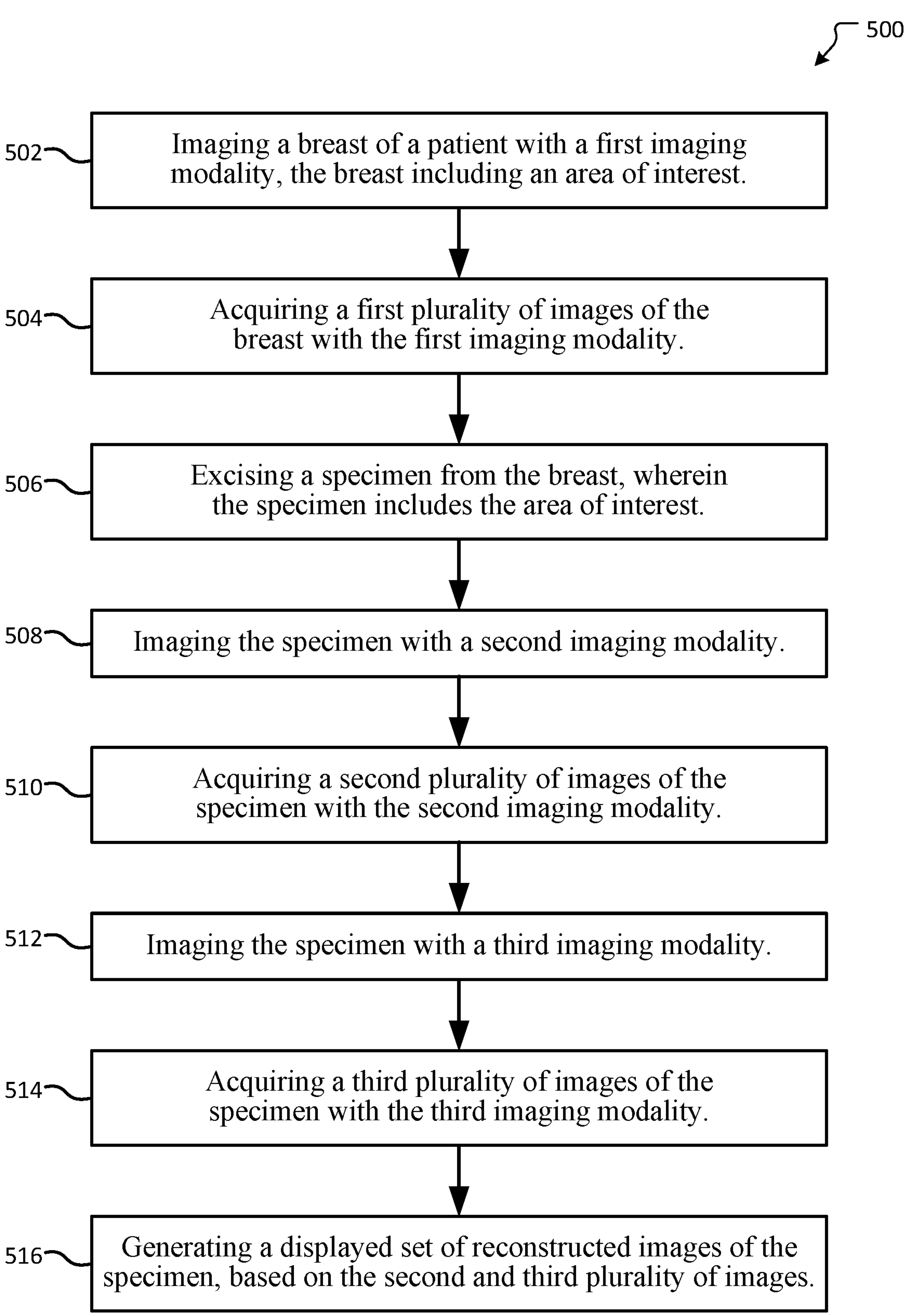
FIG. 5 illustrates another example method for multi-modality imaging of a specimen.

FIGS. 4-5 illustrate methods that may be performed by the systems described herein. In FIGS. 4-5, some of the operations may be optional. FIG. 4 illustrates a method 400 for multi-modality imaging of a specimen (e.g., with systems 100, 300, 600 described herein). Method 400 begins at operation 402 where a specimen is received on a rotatable support surface (e.g., receiving surface 112). The rotatable support surface may be coupled to a rotatable pedestal or may rotate about a pedestal (e.g., pedestal 110). The specimen may be removably coupled to the support surface, such as via gravitational and/or frictional force(s), straps, apparatuses, etc. In an example, the specimen may be secured in an apparatus capable of compressing or flattening the specimen while the specimen is coupled to the support surface. The specimen may be repositionable or reoriented relative to the support surface as required or desired. Additionally, the specimen and/or pedestal and/or rotatable support surface may include orientation markers, which may be radiopaque and/or echogenic, to indicate orientation of the specimen relative to the breast from which it was excised.

At operation 404, the specimen is rotated through a first plurality of imaging angles. When rotating the specimen, if the support surface is configured to rotate about an axis, then the specimen may be rotated about the axis through the first plurality of imaging angles. The axis may be centered with the support surface and/or the specimen. Imaging angles may be based on an angle deviation from a home position (e.g., an imaging angle between a home position P1 and a second position P2-P20 shown in FIG. 3A) and/or an angle relative to an imaging source (e.g., imaging source 130, 304).

At operation 406, while rotating the specimen through the first plurality of imaging angles, the specimen is imaged with a first imaging modality. Any imaging source may be used, such as x-ray, ultrasound, etc. If the imaging source is an x-ray source, then the first imaging modality may be selected from the group consisting of: a low-dose CT scan; a high-dose CT scan; a low-dose 2D x-ray exposure; a high-dose 2D x-ray exposure; a low-dose tomosynthesis scan; and a high-dose tomosynthesis scan. The imaging source may be disposed a fixed distance from the axis of rotation of the support surface. The axis of rotation may be movable relative to the imaging source, such as to move the support surface toward or away from the imaging source.

At operation 408, a first plurality of images are acquired with the first imaging modality. Each image of the first plurality of images is taken at a first dose at each of the first plurality of imaging angles. For example, if the first imaging modality is a low-dose tomosynthesis scan imaging at every one degree for a total sweep of 31 degrees for imaging angles −15 degrees to +15 degrees, then the first plurality of images includes 31 images taken at a low dose between the range of −15 degrees to +15 degrees.

At operation 410, the specimen is rotated through a second plurality of imaging angles. The second plurality of imaging angles may be the same or different than the first plurality of imaging angles. One or more angles of the first and second plurality of imaging angles may be the same and/or one or more angles of the first and second plurality of imaging angles may be different. In an example, the second plurality of imaging angles is a subset of the first plurality of imaging angles where the first plurality of imaging angles includes at least one angle not included in the second plurality of imaging angles. Alternatively, the first and second plurality of imaging angles may have no common angles (e.g., if the first and second plurality of images may be imaged in the same, single sweep).

At operation 412, while rotating the specimen through the second plurality of imaging angles, the specimen is imaged with a second imaging modality. Any imaging source may be used for the second imaging modality. The first and second imaging modalities may be different. Additionally, the second imaging modality may be associated with a different dose than the first imaging modality. In an example, the second imaging modality is also selected from the group consisting of: a low-dose CT scan; a high-dose CT scan; a high-dose 2D x-ray exposure; a low-dose tomosynthesis scan; and a high-dose tomosynthesis scan. In an example, the first and second imaging modalities may be selected from the aforementioned group. Alternatively, the first and second imaging modalities may make up a single-sweep CT scan or a single-sweep tomosynthesis scan where the first plurality of imaging angles are a first portion of the sweep associated with a first dose and the second plurality of imaging angles are a second portion of the sweep associated with a second dose. For example, if the second imaging modality is a high-dose tomosynthesis scan imaging at every one degree for a total sweep of 15 degrees for imaging angles −7.5 degrees to +7.5 degrees, then the first plurality of images includes 15 images taken at a high dose between the range of −7.5 degrees to +7.5 degrees.

At operation 414, a second plurality of images of the specimen are acquired with the second imaging modality. Any or all of operations 410-414 may occur concurrently with, prior to, or subsequently to any or all of operations 404-408.

At operation 416, a set of reconstructed images of the specimen are generated based on both the first plurality of images and the second plurality of images. When generating the set of reconstructed images, image data from images taken at a higher dose may be used to reconstruct at least a portion of the set of reconstructed images containing a micro-calcification. Additionally or alternatively, at least one image of the set of reconstructed images may be used to identify and/or evaluate a margin of the specimen about a lesion. The lesion may also be identified based on the set of reconstructed images. Additionally or alternatively, at least one reconstructed image of the set of reconstructed images may be displayed (e.g., on display 126).

In examples, imaging at a first plurality of imaging angles is used to generate a first plurality of images and imaging at a second plurality of imaging angles is used to generate a second plurality of images. Both the first plurality of images and the second plurality of images may be used to generate calcification-enhanced images and used to generate lesion-enhanced images. Thus, the first plurality of images and the second plurality of images may be used to generate a plurality of sets of reconstructed images (e.g., a first set that is calcification-enhanced and a second set that is lesion-enhanced or mass-enhanced).

FIG. 5 illustrates another method 500 for multi-modality imaging of a specimen (e.g., with the systems 100, 300, 600 described herein). Method 500 begins at operation 502 where a breast of a patient, including an area of interest (e.g., lesion, which may be a mass or micro-calcification, etc.) of the breast, is imaged with a first imaging modality. Imaging the breast with the first imaging modality may assist a medical professional in identifying and/or localizing the area of interest prior to excision or biopsy of the area of interest. Imaging of the breast may vary from imaging of the specimen. For example, while the specimen may be freely rotated relative to an image source, the image source is instead often moved relative to the breast tissue. For example, a breast imaging system (that may be capable of MMI, e.g., mammogram and tomosynthesis breast imaging techniques) is available from Hologic, Inc., under the brand name SELENIA® DIMENSIONS®. Additionally, imaging of the breast is used to identify, localize, and/or confirm biopsy of an area of interest, while imaging of an excised specimen containing the area of interest is instead used to identify and/or evaluate appropriate or desired margins to determine if additional breast tissue should be removed.

At operation 504, a first plurality of images of the breast is acquired with the first imaging modality. The first imaging modality may be any imaging type or modality (e.g., x-ray, ultrasound, CT, fluoroscopy, etc.). The first plurality of images may be acquired using a first imaging source. To acquire the first plurality of images, the first imaging source may move relative to the breast. For example, the first imaging source may rotate about or around the breast at a fixed radius to obtain the first plurality of images. The first plurality of images may be used to assist a medical professional in a localization procedure to localize the area of interest for excision.

At operation 506, a specimen, including a portion of the area of interest, is excised from the breast. The specimen may be excised based on the localization procedure described at operation 504, which may be based on the first plurality of images.

At operation 508, the specimen is imaged with a second imaging modality. Operation 508 may be similar to operations 404-406 in method 400. For example, the specimen may be rotated through a second plurality of imaging angles. While rotating the specimen through the second plurality of imaging angles, the specimen may be imaged with the second imaging modality. A second imaging source may be used to image the specimen with the second imaging modality. The second imaging source may be a different type than the first (e.g., the first imaging source may emit an ultrasonic beam and the second imaging source may emit an x-ray beam) and/or may be a different source as associated with a different imaging system (e.g., the first imaging source associated with a breast imaging system and the second imaging source associated with a specimen imaging system). At operation 510, a second plurality of images of the specimen is acquired with the second imaging modality.

At operation 512, the specimen is imaged with a third imaging modality. Operation 512 may be similar to operations 410-412 in method 400. For example, the specimen may be rotated through a third plurality of imaging angles. While rotating the specimen through the third plurality of imaging angles, the specimen may be imaged with the third imaging modality. A third imaging source may be used to image the specimen with the third imaging modality. The third imaging source may be a different type than the first and/or second imaging source and/or may be a different source as associated with a different imaging system (e.g., a breast imaging system or a specimen imaging system). The third imaging source may be the same or different as the first imaging source and/or the second imaging source. At operation 514, a third plurality of images of the specimen is acquired with the third imaging modality.

At operation 516, a displayed set of reconstructed images of the specimen are generated. The set of reconstructed images may be based on both the second and third plurality of images. At least one image of the set of reconstructed images may be used to identify and/or evaluate a margin of the specimen. Based on the margin, additional breast tissue may be excised from the breast. As further described herein, the specimen may include one or more orientation markers or orientation indicators to orient the specimen relative to the breast from which it was excised. Additional excision of breast tissue may be further based on the orientation marker/indicator.

Figure 6:
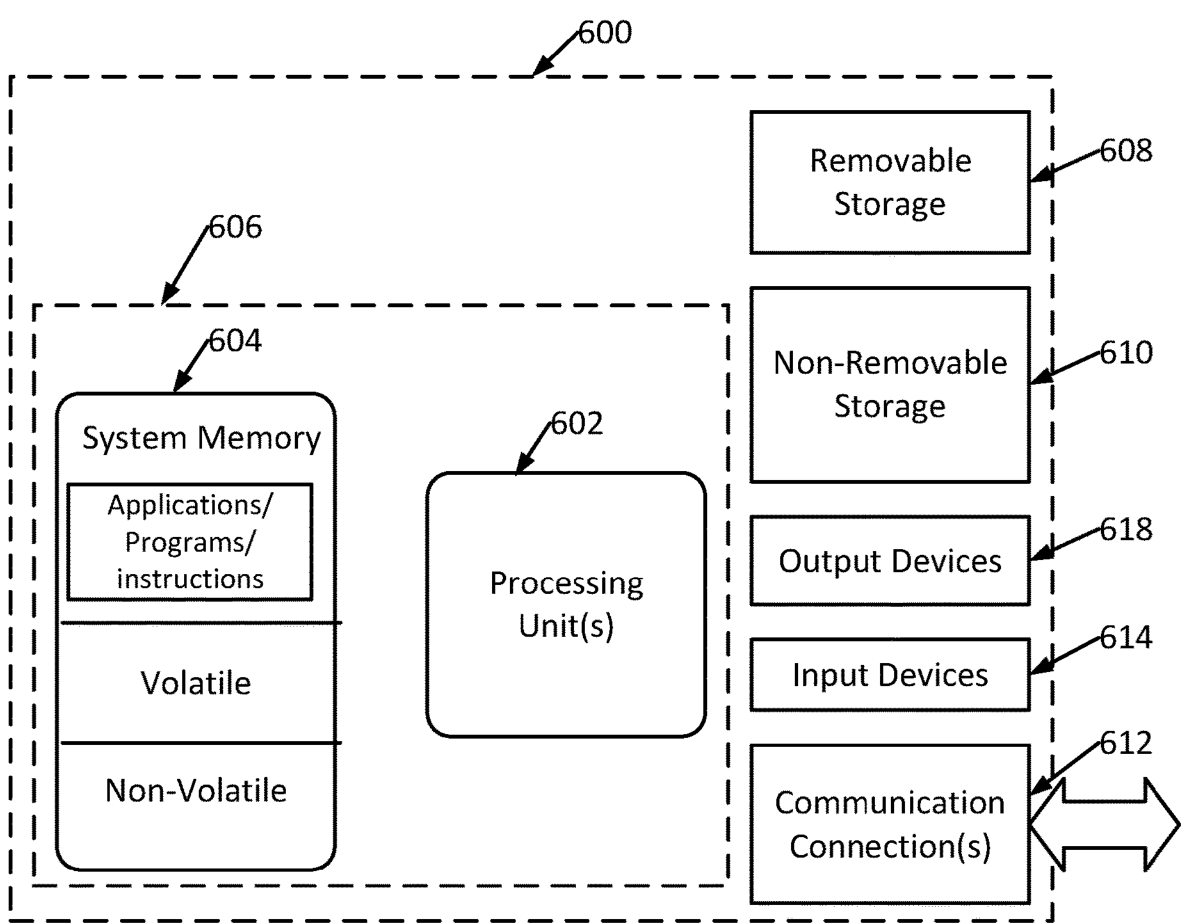
FIG. 6 illustrates an exemplary suitable operating environment for a specimen imaging system.

FIG. 6 illustrates an exemplary suitable operating environment 600 for a specimen imaging system described herein. In its most basic configuration, operating environment 600 typically includes at least one processing unit (or processor) 602 and memory 604. Depending on the exact configuration and type of computing device, memory 604 (storing, instructions to perform projection of an image onto a specimen) may be volatile (such as RAM), non-volatile (such as RAM, flash memory, etc.), or some combination of the two. This most basic configuration is illustrated in FIG. 6 by dashed line 606. Further, environment 600 may also include storage devices (removable, 608, and/or non-removable, 610) including, but not limited to, magnetic or optical disks or tape. Similarly, environment 600 may also have input device(s) 614 such as keyboard, mouse, pen, voice input, etc. and/or output device(s) 616 such as a display, speakers, printer, etc. Also included in the environment may be one or more communication connections 612, such as LAN, WAN, point to point, etc. In embodiments, the connections may be operable to facility point-to-point communications, connection-oriented communications, connectionless communications, etc.

Operating environment 600 typically includes at least some form of computer readable media. Computer readable media can be any available media that can be accessed by processing unit (or processor) 602 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, microwave, and other wireless media. Combinations of the any of the above should also be included within the scope of computer readable media.

The operating environment 600 may be a single computer operating in a networked environment using logical connections to one or more remote computers. The remote computer may be a personal computer, a server, a router, a network PC, a peer device or other common network node, and typically includes many or all of the elements described above as well as others not so mentioned. As an example, the operating environment 600 may be shared between one or more imaging systems, such as a breast imaging system and a specimen imaging system (e.g., systems 100, 300). As another example, each imaging system (e.g., breast imaging system and specimen imaging system) may each have a unique operating environment 600. As a further example, the operating environment 600 may be shared between multiple breast imaging system(s) and/or multiple specimen imaging system(s). The logical connections may include any method supported by available communications media. Such networking environments are commonplace in offices, enterprise-wide computer networks, intranets and the Internet.

As should be appreciated, while the above methods have been described in a particular order, no such order is inherently necessary for each operation identified in the methods. For instance, the operations identified in the methods may be performed concurrently with other operations or in different orders. In addition, the methods described above may be performed by the systems described herein. For example, a system may have at least one processor and memory storing instructions that, when executed by the at least one processor, cause the system to perform the methods described herein.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

Although aspects of the present disclosure are described with respect to image analysis of excised breast tissue, it should be appreciated that the present disclosure may also be useful in variety of other applications where a plurality of imaging modes may improve image quality and/or efficiency of a specimen, tissue, bone, living organism, body part, or any other object, living or dead.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art. Further, as used herein and in the claims, the phrase "at least one of element A, element B, or element C" is intended to convey any of: element A, element B, element C, elements A and B, elements A and C, elements B and C, and elements A, B, and C.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A method for imaging a specimen, the method comprising:

receiving a specimen on a rotatable support surface disposed within an imaging cabinet, wherein the support surface is configured to rotate about an axis;

rotating the specimen about the axis through a first plurality of imaging angles;

while rotating the specimen through the first plurality of imaging angles, imaging the specimen with a first imaging modality using an x-ray imaging source within the imaging cabinet, wherein the x-ray imaging source is disposed a fixed distance from the axis, and wherein the first imaging modality is associated with a low x-ray dose;

acquiring a first plurality of images of the specimen with the first imaging modality;

rotating the specimen through a second plurality of imaging angles;

while rotating the specimen through the second plurality of imaging angles, imaging the specimen with a second imaging modality using the x-ray imaging source, wherein the second imaging modality is associated with a high x-ray dose;

acquiring a second plurality of images of the specimen with the second imaging modality, wherein the second imaging modality is different than the first imaging modality, and wherein at least some of the first plurality of imaging angles are encompassed within the second plurality of imaging angles; and generating a set of reconstructed images of the specimen, wherein the set of reconstructed images is based on both the first plurality of images and the second plurality of images.

2. The method of claim 1, the method further comprising: securing the specimen to the support surface.

3. The method of claim 1, wherein the imaging the specimen with the second imaging modality occurs subsequent to the imaging the specimen with the first imaging modality.

4. The method of claim 1, wherein the second plurality of images acquired with the second imaging modality associated with the high x-ray dose depict a microcalcification.

5. The method of claim 1, wherein the first plurality of imaging angles includes at least one angle not included in the second plurality of imaging angles.

6. The method of claim 1, the method further comprising: evaluating a margin of the specimen based on the set of reconstructed images.

7. The method of claim 1, the method further comprising: displaying at least one reconstructed image of the set of reconstructed images.

8. The method of claim 1, wherein the first imaging modality and the second imaging modality are selected from the group consisting of:

a low-dose CT scan;

a high-dose CT scan;

a high-dose 2D x-ray exposure;

a low-dose tomosynthesis scan; and a high-dose tomosynthesis scan.

9. The method of claim 1, wherein the first imaging modality is one of a low-dose CT scan or a low-dose tomosynthesis scan, and wherein the second imaging modality is one of:

a high-dose CT scan;

a high-dose 2D x-ray exposure; and a high-dose tomosynthesis scan.

10. The method of claim 8, wherein the rotating the specimen through the first plurality of imaging angles and the rotating the specimen through the second plurality of imaging angles is performed in a single sweep.

11. The method of claim 10, wherein the first imaging modality is the low-dose CT scan and the second imaging modality is the high-dose CT scan.

12. The method of claim 10, wherein the first imaging modality is the low-dose tomosynthesis scan and the second imaging modality is the high-dose tomosynthesis scan.

13. A method for imaging a specimen, the method comprising:

imaging a breast of a patient with a first imaging modality, the breast including an area of interest;

acquiring a first plurality of images of the breast with the first imaging modality;

excising a specimen from the breast, wherein the specimen includes at least a portion of the area of interest;

placing the specimen within an interior chamber of an imaging cabinet having an x-ray source;

imaging the specimen via the x-ray source with a second imaging modality associated with a low x-ray dose;

acquiring a second plurality of images of the specimen with the second imaging modality, wherein the second plurality of images are acquired around a second plurality of imaging angles;

imaging the specimen via the x-ray source with a third imaging modality associated with a high x-ray dose;

acquiring a third plurality of images of the specimen with the third imaging modality, wherein the third plurality of images are acquired around a third plurality of imaging angles, at least some of the second plurality of imaging angles are encompassed within the third plurality of imaging angles, and wherein the third imaging modality is different than the second imaging modality; and generating a displayed set of reconstructed images of the specimen, wherein the displayed set of reconstructed images is based on both the second plurality of images and the third plurality of images.

14. The method of claim 13, wherein the first imaging modality is an ultrasound.

15. The method of claim 13, the method further comprising:

identifying a margin of the specimen; and removing additional breast tissue based on the identified margin.

16. The method of claim 13, wherein imaging the breast of the patient with the first imaging modality uses a first imaging source, and wherein imaging the specimen with the second imaging modality and the third imaging modality use a second imaging source.

17. The method of claim 13, wherein the second plurality of imaging angles includes at least one angle that is not included in the third plurality of imaging angles.

18. An apparatus for imaging a specimen, the apparatus comprising:

a housing defining an interior chamber;

a pedestal disposed within the interior chamber of the housing, wherein the pedestal is configured to support a specimen and rotate about an axis;

an x-ray imaging source disposed within the housing, the x-ray imaging source configured to project a beam inside the interior chamber;

a processor;

memory storing instructions that, when executed by the processor, cause the apparatus to perform a set of operations comprising:

rotating the pedestal about the axis through a first plurality of imaging angles;

while rotating the pedestal through the first plurality of imaging angles, imaging with a first imaging modality using the x-ray imaging source, wherein the x-ray imaging source is disposed a fixed distance from the axis, and wherein the first imaging modality is associated with a low x-ray dose;

acquiring a first plurality of images with the first imaging modality;

rotating the pedestal about the axis through a second plurality of imaging angles, while rotating the pedestal through the second plurality of imaging angles, imaging with a second imaging modality using the x-ray imaging source, wherein the second imaging modality is associated with a high x-ray dose;

acquiring a second plurality of images with the second imaging modality, wherein the second imaging modality is different than the first imaging modality, and wherein at least some of the first plurality of imaging angles are encompassed within the second plurality of imaging angles; and generating a set of reconstructed images based on both the first plurality of images and the second plurality of images.

19. The apparatus of claim 18, wherein the apparatus further comprises a display and wherein the set of operations further comprises:

displaying an image of the set of reconstructed images.

* * * * *